United States Patent [19]

Ibsen et al.

[11] Patent Number: 4,964,911
[45] Date of Patent: Oct. 23, 1990

[54] ADHESIVE BONDING OF ACRYLIC RESINS, ESPECIALLY IN DENTISTRY

[75] Inventors: Robert L. Ibsen, Santa Maria; William R. Glace, Orcutt, Donald R. Pacropis, Santa Maria, all of Calif.

[73] Assignee: Den-Mat Corporation, Santa Maria, Calif.

[21] Appl. No.: 285,502

[22] Filed: Dec. 16, 1988

Related U.S. Application Data

[63] Continuation-in-part of Ser. No. 107102, Oct. 13, 1987, abandoned.

[51] Int. Cl.$^5$ .................. A61C 13/23; A61K 6/08
[52] U.S. Cl. .................. 106/35; 260/998.11; 433/228.1; 523/116; 523/118
[58] Field of Search .................. 106/35; 523/116, 118, 523/120; 260/998.11; 433/228.1

[56] References Cited

U.S. PATENT DOCUMENTS

| 4,514,527 | 4/1985 | Bowen | 523/115 |
| 4,521,550 | 6/1985 | Bowen | 523/116 |
| 4,540,722 | 9/1985 | Bunker | 523/109 |
| 4,588,756 | 5/1986 | Bowen | 523/116 |
| 4,659,751 | 4/1987 | Bowen | 523/116 |

*Primary Examiner*—Paul Lieberman
*Assistant Examiner*—Linda D. Skaling

*Attorney, Agent, or Firm*—Owen, Wickersham & Erickson

[57] ABSTRACT

A bonding adhesive for dentistry and a method for preparing the surface of dentin, enamel, or other natural or industrial substrates containing or capable of binding metallic ions, for adhesion of composite materials or resins. First, an aqueous solution of phosphoric acid or a mixture of phosphoric and nitric acids along with aluminum oxalate, or phosphoric acid alone, is applied to the surface. Second, a solution comprising a solvent and at least one compound selected from the group consisting of (1) N-phenylglycine in a mixture with the alkali metal salt of N-phenylglycine, (2) a mixture of the adduct of the alkali salts N(p-tolyl)glycine and glycidyl methacrylate, with the mixture N(p-tolyl)glycine and glycidyl methacrylate (3) the addition reaction product of the alkali metal salt of N-phenylglycine and glycidyl methacrylate, and N-phenylglycine, N(p-tolyl) glycine, N-phenylalanine, sarkosine, N-laurylsarkosine, glycine, N,N-dimethylglycine, 3(N-phenyl) amino propionic acid, 3(N-p-tolyl) amino propionic acid, omega-amino fatty acids, N-substituted-omega-amino fatty acids, the addition reaction product of N-phenyl glycine and glycidyl reagents, the reaction product of N(substituted phenyl) glycine and glycidyl reagents, and other amino acids; is applied to the surface. Third, a solution of PMDM is applied to the surface.

44 Claims, No Drawings

ADHESIVE BONDING OF ACRYLIC RESINS, ESPECIALLY IN DENTISTRY

This is a continuation-in-part of application Ser. No. 107,012, filed Oct. 13, 1987, now abandoned.

BACKGROUND OF THE INVENTION

1. Field of the Invention

This invention relates to improved methods and materials for providing adhesive bonding of acrylic resins to industrial, natural, and dental substrates, and more particularly to dental restoration methods and methods of improving adhesion of dental composite restoratives to dentin. More specifically, methods and materials for strong adhesive bonding of composite resins to dentin are disclosed with the objects of improving the treatment of cervical erosions, root caries, and other dental conditions, eliminating much of the mechanical cutting of dentin and enamel currently required for mechanical retention of restorations.

2. Description of the Prior Art

For many years, advances in the study of methods of adhesive bonding of composite materials to hard tooth tissues have evolved in small increments. Swiss Patent No. 687,299 to deTrey, Inc. described a material for bonding to dentin. A more recent patent, U.S. Pat. No. 4,540,722 to 3M Company describes a modification of the original deTrey material. U.S. Pat. Nos. 4,514,527; 4,521,550; 4,588,756; and 4,659,751 all to R. L. Bowen, assigned to the American Dental Association Health Foundation, disclose more recent developments based on the use of mordants and adhesion promoting coupling agents. Each of these steps has resulted in incremental improvements in bonding to dentin, to the point where it is presently feasible for the dentist to use adhesive bonding to retain composite restorations.

The prior art closest to the present invention is the Bowen U.S. Pat. No. 4,659,751, which preferably employed a two-step technique. This technique comprised, first, treating the surface to be bonded with an acidic solution preferably containing nitric or other strong acid, polyvalent cations, and compounds such as oxalic acid or other polyfunctional acids which can form relatively water-insoluble precipitates with calcium and other polyvalent cations at pH values above that of the acidic aqueous treatment solution, and also containing at least one compound selected from the group consisting of (1) N-phenylglycine ("NPG"), (2) the adduct of N(p-tolyl)glycine and glycidyl methacrylate ("NTG-GMA"), (3) the addition reaction product of N-phenylglycine and glycidyl methacrylate ("NPG-GMA"), and (4) other amino acids. Second, the technique called for applying a solution containing at least one monomeric compound selected from the group consisting of (1) the addition reaction product of pyromellitic acid dianhydride and 2-hydroxyethyl methacrylate ("PMDM"), (2) the addition reaction product of 3,3',4,4'-benzophenonetetracarboxylic dianhydride and 2-hydroxyethyl methacrylate ("BTDA-HEMA"), and (3) 4-methacryloxyethyltrimellitic anhydride ("4-META").

Alternatively, but less preferred, in the case of vital dentin, according to the Bowen U.S. Pat. No. 4,659,751, the surface to be treated could be contacted with a strongly acidic solution, but still containing NPG, NTG-GMA, NPG-GMA, and/or other amino acids, followed by contacting with PMDM, BTDA-HEMA and/or 4-META monomer solution. Also, an acidic solution and the NPG or other amino acid solution could be applied separately, one after the other (instead of as a combined solution) before the PMDM or other monomer is applied. The components for practicing the method of this Bowen invention are said to be conveniently made available in the form of a kit or article of manufacture described in that patent.

A particularly preferred method of the Bowen invention of U.S. Pat. No. 4,659,751 is accomplished by treating the surface of the dentin, enamel or other substrate containing or capable of binding metallic ions with a solution with contains (1) at least one salt of a polyvalent cation which can bind to substrate surface sites; (2) a compound which contains at least one acid group and preferably two or more acidic groups (3) a strong acid; and (4) at least one surface-active compound selected from the group consisting of NPG, alpha or beta amino acids, and other compounds, each of which contain at least one of each of the following groups: carboxyl and amino. The surface-active compound may be a surface-active comonomer which contains a moiety capable of free radical polymerization as well as the carboxyl and amino groups. The resultant substrate surface is then treated with a solution which contains at least one compound selected from the group consisting of (1) PMDM, (2) BTDA-HEMA, (3) 4-META, (4) other compounds containing at least one group or moiety capable of free radical polymerization, and at least one aromatic ring or moiety containing, electron-withdrawing substituents which do not interfere with free radical polymerization, and which compound preferably also contains one or more free carboxyl groups, or anhydride groups which can form free carboxyl groups upon hydrolysis, and (5) camphoroquinone.

SUMMARY OF THE INVENTION

The present invention comprises the use of certain alternative materials—especially the alkali metal salts of NPG, NPG-GMA, and NTG-GMA and mixtures thereof with NPG, NPG-GMA or NTG-GMA—with the other ingredients specified by the Bowen patent U.S. Pat. No. 4,659,751. It also comprises the use of simplified methods. The present invention produces even stronger adhesive bonds between composite materials or resin and dentin and also results in effective bonding between these materials or resin and enamel and other natural or industrial substrates. There is also greater color stability in the resultant composition than was previously achieved.

An advantage of this invention is that it provides better materials and methods which make it easier to obtain aesthetic adhesive bonding of composite and unfilled resins of the type polymerized by free radicals to dentin, enamel, industrial substrates, and/or other substrates containing or capable of binding metallic ions (i.e., ions of elements on the left side and in the center of the periodic table). The resulting products are also within the scope of this invention.

Some of the materials disclosed in the present invention replaced a much more expensive material used in some of the previous patents.

It has recently been discovered that what has been furnished as the sodium salt of NTG-GMA is really a mixture of the NGT-GMA with the sodium salt. The two are at equilibrium, not only about 50% of each but varying from 40% of one ingredient and 60% of the other to 60% of the one ingredient and 40% of the other. It had been thought that material was the sodium salt of NTG, but recent information has come that that was a mistake and that the correct analysis showed the two ingredients mixed together in equivalent amounts; so that they would be roughly 50:50 in proportion, but not exactly. The mixture of the acid and the sodium salt has special benefits that have been noted and were attributed to the pure sodium salt. However, when the device was first purified, transforming all the portion that was the sodium salt into the substantially pure NTG and when material was converted back to the sodium salt, results were different. Therefore, the results apparently follow from the use of a mixture of the acid with the sodium salt.

The present invention may be summarized as follows:

First, pretreating the dentin with an acidic solution preferably containing a strong acid (such as nitric acid, phosphoric acid, or a mixture of phosphoric and nitric acids) which may also contain polyvalent cations, and compounds such as oxalic acid or other polyfunctional acids which can form relatively water-insoluble precipitates with calcium and other polyvalent cations at pH values above that of the aqueous treatment solution.

Second, applying a solution containing an alkali metal salt of one of the group consisting of (1) N-phenyl glycine ("NPG"), (2) the adduct of N-(p-tolyl) glycine and glycidyl methacrylate ("NTG-GMA"), (3) the addition reaction product of N-phenylglycine and glycidyl methacrylate ("NPG-GMA"), and (4) other amino acids. This solution is in a solvent composed of a mixture of water and a polar organic solvent, such as acetone. This solution may contain, in addition to the alkali metal salt, an approximately equal amount of the actual NPG, NTG-GMA, NPG-GMA or the amino acids used in the salt.

Third, a solution is applied which contains at least one monomeric compound selected from the group specified by Bowen, preferably the addition reaction product of pyromellitic acid dianhydride and 2-hydroxyethyl methacrylate ("PMDM").

A combined solution containing both the (a) alkali metal salt of the amino acid, or amino acid adduct or reaction product (as stated in the "second" solution above and the acid or adduct or addition reaction product as in the "second" solution, and (b) the PMDM may be applied, rather than applying each solution separately, the results may be less satisfactory or more satisfactory.

The components for practicing the method of the invention may be commonly made available in the form of a kit or article of manufacture.

DESCRIPTION OF A PREFERRED EMBODIMENT

The preferred method for preparing the substrate surface for adhesion of composite materials and resins comprises contacting the surface with three separate solutions, one after the other.

The first solution

The first solution comprises (1) a strong acid or combination of acids and may include (2) one or more polyvalent cations (preferably $Al^{+++}$) which can form relatively water-insoluble precipitates with phosphate ions.

The preferred polyvalent cation, when used, is the trivalent aluminum ion, at least as to dental applications where aesthetics is important. Aluminum oxalate gives excellent results. The ferric ion, while usable in some applications, can lead to staining by reduction to ferrous ion in the presence of sulfide. The ferrous sulfide can be generated by the metabolic activity of anaerobic microorganisms. However, sulfides do not form black complexes with aluminum ions under the conditions of interest Although literature references list aluminum oxalate as insoluble in water, it has been discovered by others, including Bowen, that aluminum oxalate is soluble in water when formulated with the other ingredients of the present invention. The solubility of aluminum oxalate in water depends upon the stoichiometry and pH. Aluminum oxalate does not precipitate from the aqueous solution of the present invention. Aluminum ions can form insoluble, metastable, microporous, quasi-amorphous precipitates of phosphate surfaces. Aluminum ions can strengthen the altered substrate surface structures by crosslinking and reinforcing the collagenous component of dentin surface reacted upon by the first aqueous solution of the present invention.

In applications where color stability and aesthetics are not deciding factors, aluminum ions, ferric ions, and other polyvalent cations can be used separately or in combinations in the first aqueous solution of the present invention.

An important function of the precipitation of one or more polyvalent cations with phosphate ions and/or collagenous and/or organic components is thought to be the occluding or obturating of dential tubules in vital dentin, so as to protect the odontoblasts and pupal tissues from ingress of foreign matter.

The function of the incorporation of a compound with one or more carboxyl groups, such as, for example, oxalic acid or an "oligocarboxylic acid" as exemplified by aluminum oxalate, is believed to be the precipitation of insoluble calcium and the other complexes which also can assist in obturating the dential tubules of vital dentin, when it is treated with the first aqueous solution of the present invention.

The strong acid which is also preferably present in the first aqueous treatment solution renders the solution low in pH value. The purposes of the low pH are (1) to dissolve the smeared (disturbed) surface layer on cut dentin, enamel, or other substrates, (2) to partially decalcify intertubular dentin, (3) to remove pellicle, plaque, or other surface contaminants from the substrate, and (4) to "acid etch" enamel and other substrate surfaces. Another function of the strong acid component which renders the first aqueous solution strongly acidic (low pH) is to render soluble some or all of the other components in the aqueous solution The preferred acids for use in the method aqueous of this invention is phosphoric acid, or a mixture of phosphoric and nitric acids, ranging in concentration from about one-tenth percent to about 50% by weight, preferably, from about 0.1% to 10% by weight and most preferably on the order of about 2 to 5% by weight of the aqueous solution. It has been discovered that compounds such as $Al(NO_3)_3$ can hydrolyze in the aqueous formulation of the first solution to provide the strong acid and necessary low pH. Such strong acids as hydrochloric acid, perchloric acid, sulfuric acid and others, and acid mixtures may or may not be effective in improving the bond strengths obtainable in the use of the present invention.

The second solution

The second solution comprises a solution in an acetone/water solvent of the sodium or other alkali metal salt of (1) N-phenylglycine or NPG (e.g., NaNPG), (2) the adduct of N-phenylglycine-glycidyl methacrylate (e.g., NaNPG-GMA), or (3) N-tolylglycine-glycidylmethacrylate e.g., NaNTG-GMA) either alone or with the NPG, NPG-GMA, or NTG-GMA. It appears that the crude material thought originally to be a sodium salt of NPG, NPG-GMA, or NTG-GMA has recently been found to be actually a mixture of the NPG, NPG-GMA, or NTG-GMA with the sodium salt of the same, varying between the values of 40–60 to 60–40 of the respective ingredients and being closer to a 50–50 mixture. The commercial product is not pure, either as an acid or as the sodium salt, without special treatment. The water content of the acetone/water solvent is preferably between about 15% and about 50%. The total content of the NaNTG-GMA mixture with NTG-GMA is between about 1% and about 10%, as may be the NaNPG and NPG or NaNPG-GMA and NPG-GMA content, the remainder being the solvent.

Although the specific function of the NaNTG-GMA (or NaNPG or NaNPG-GMA) in the present invention has not been ascertained, it is essential in obtaining the necessary high bond strengths. It may be speculated that it is surface-active, that it forms complexes with cations, absorbs on the nascent surfaces formed within the substrate structures, and that it plays a role in the initiation of polymerization of compounds laid down in later steps.

The alkali-metal salts of the amino acids and/or their complexes as used are essential to this invention for two reasons—significantly stronger bonds are formed than with NPG, NPG-GMA, or NTG-GMA, alone, and the material is much less costly to manufacture than where pure NPG, NPG-GMA, and NTG-GMA are used, instead of the sodium or other alkali metal salt thereof.

Additional examples of alkali metal salts containing at least one amino group and at least one carboxyl group include the alkali metal salts or esters of: the amino acids in general, N-phenylglycine, N(p-tolyl)glycine, N-phenylalanine, sarkosine, N-lauroylsarkosine, glycine, N,N-dimethylglycine, 3(N-phenyl) amino propionic acid, 3(N-p-tolyl) amino propionic acid, omegaamino fatty acids, N-substituted -omega-amino fatty acids, the addition reaction product of N-phenyl glycine and glycidyl reagents, and the reaction product of N(substituted phenyl) glycine and glycidyl reagents.

It is anticipated that the alkali-metal salts of many or all of these compounds would be effective to one degree or another.

The third solution

The third solution contains a solution of PMDM at a percentage of between 1% and 25%, the solvent being acetone with a water content of from 0% to about 25%. PMDM is the addition reaction product of pyromellitic acid dianhydride and 2 moles of 2-hydroxyethyl methacrylate. While the structure(s) of PMDM are not definitely known, and it is best characterized as the above-recited addition reaction product, the structures of the two isomers of PMDM are postulated to be as follows:

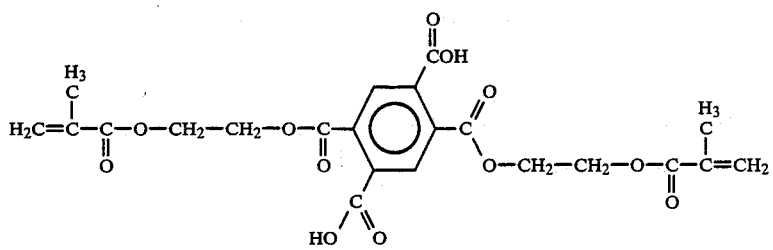

PMDM

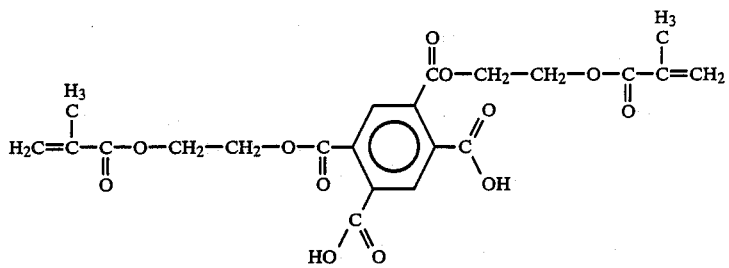

The PMDM isomer may be applied to the dentin or enamel surface in any desired proportions, dissolved in a solvent or a mixture of solvents. Again, the preferred solvent is acetone, although other solvents may be used. A solution of PMDM in acetone is efficacious, although other concentrations, preferably in a range of about 0.1% to a saturated solution, may be used.

Preferably, the excess solution of PMDM is not removed, but rather, the solvent is removed by evaporation that may be speeded by applying a gentle stream of air at any feasible temperature.

A kit of ingredients

Advantageously, the components necessary to effect the method of this invention may be packaged in an article or manufacture of "kit" for use by the dentist.

For application after the dentin is prepared as described above, a mix of composite or unfilled resin may be applied. Adhesion tests utilizing extracted human and bovine teeth indicated strong adhesive bonding when utilizing the most preferred embodiments of the invention, as shown in Table 1 below.

Although the formulations shown in Table 1 do not necessarily represent optimized proportionalities of the ingredients, the data indicate that very strong adhesive bonding can be obtained with various proportions, concentrations, and recipes for the preparation of the solutions. Here, as an example, the same amount of each of the three solutions is used.

TABLE 1

Sheer Stress Adhesive Strengths of a Composite Bonded to Treated Surfaces

| Solution 1 | Solution 2 | Solution 3 | Average Adhesion psi |
|---|---|---|---|
| $Al_2(C_2O_4)_3/HNO_3$ | 10% equilibrium mixture of NaNTG-GMA with NTG-GMA | 5% PMDM | 965 |
| $Al_2(C_2O_4)_3/HNO_3$ | 5% equilibrium mixture of NaNTG-GMA with NTG-GMA | 20% PMDM | 1035 |
| $Al_2(C_2O_4)_3/HNO_3$ | 5% equilibrium mixture of NaNTG-GMA with NTG-GMA | 5% PMDM | 936 |
| $Al_2(C_2O_4)_3/HNO_3$ | 5% equilibrium mixture of NaNTG-GMA with NTG-GMA | 10% PMDM | 1140 |

Table 2 lists bond strengths obtained by the same test method when state-of-the-art commercial dentin adhesives are utilized with the same composite recommended by the manufacturers.

TABLE 2

Sheer Stress Adhesive Strengths of Composites Bonded to Treated Dentin Surfaces

| Dentin Surface Treatment Material | Average Adhesion (psi) |
|---|---|
| Scotchbond | 428 |
| Dentin Adhesit | 465 |
| Bondlite | 645 |
| Universal Bond | 285 |
| Creation 3-in-1 | 490 |
| GLUMA* | 249 |
| Tenure** | 938 |

*Not commercially available in U.S.
**Similar to invention but using NTG-GMA alone in Solution 2 instead of the mixture of the sodium salt of NTG-GMA with NTG-GMA.

EXAMPLE 1

Significance of omission of polyvalent metal carboxylate in the first solution

Five extracted teeth were ground to give a flat surface of dentin. An aqueous solution of 2.5% $HNO_3$ was applied for 60 seconds, then rinsed away with water and the surface dried. No polyvalent metal carboxylate was used. Next, a 10% solution of NPG-GMA in acetone was applied and allowed to dry, followed by a solution of 5% PMDM in acetone, A cylinder of a commercially available light-cured dental composite was bonded to the surface and tested to failure in sheer after 15 minutes in water. The average bond strength was 1454 psi in these However, the above experiment was repeated with samples stored three days in water at 37° C. until testing. Then, the bond strength dropped to 600 psi, illustrating that the absence of carboxylate ions in the first nitric acid solution greatly affected the bond strength to well-wet teeth, which correspond closely to teeth in the mouth.

EXAMPLE 2

Significance of omission of the second solution

Five extracted teeth were ground to give a flat dentin surface. Each was treated with a solution of aluminum oxalate $(Al_2(C_2O_4)_3)$ for 60 seconds, after which the solution was rinsed away and the surface air dried. NO second solution (as defined in Table 1) was used. Next, a solution of 5% PMDM in acetone (the third solution of Table 1) was applied and allowed to dry. A cylinder of dental composite was bonded to the treated surface. The samples were stored in water at 37° C. for one week and tested in sheer until failure. The average bond strength was 468 psi, illustrating that a surface-active monomer is necessary for optimum bonding.

EXAMPLE 3

Use of the present invention includes 10% of a mixture NaNTG-GMA with NTG-GMA as an equilibrium mixture and 5% PMDM Ten bovine teeth were ground to a flat dentin surface. Each was painted with a solution of $Al_2(CO_2O_4)_3$ in 2.5% nitric acid, which was allowed to remain for 60 seconds, then washed away and dried. Next a solution of 10% mixture of NaNTG-GMA with NTG-GMA in 85/15 acetone/water was applied and allowed to dry. There is from 40% NaNTG-GMA and 60% NTG-GMA to 60% NaNTG-GMA and 40% NTG-GMA. Finally, a solution of 5% PMDM was applied and allowed to dry. A cylinder of light-cured dental composite was applied to the treated surface and cured in place.

These samples were stored in distilled water at 37° C. for four hours, then stressed in sheer until failure. Bond strengths averaged 904 psi with a standard deviation of 250 psi—much better than in Examples 1 and 2.

EXAMPLE 4

Use of 5% of the mixture of NaNTG-GMA with NTG-GMA and 5% PMDM

Twelve samples were prepared as in Example 3 with the exception that the treating solutions were 5% NaNTG-GMA and 5% PMDM. Bond strengths averaged 824 psi with a standard deviation of 153 psi.

EXAMPLE 5

Use of 5% of the mixture of NaNTG-GMA with NTG-GMA and 10% PMDM

Thirty-three bovine teeth were prepared as in Example 3 except that the treating solutions were 5% of a mixture of NaNTG-GMA with NTG-GMA and 10% PMDM. Bond strengths averaged 764 psi with a standard deviation of 203 psi.

EXAMPLE 6

Use of 5% of a mixture of NaNTG-GMA with NTG-GMA and 20% PMDM

Twenty-nine bovine teeth were prepared as in Example 5 except that PMDM concentration was 20%. Bond strengths were an average of 1087 psi and a standard deviation of 249 psi.

EXAMPLE 7

Ten bovine teeth were prepared as in Example 5. Storage in 37° C. water was maintained for 24 hours instead of 4 hours. Bond strengths were an average of 655 psi with a standard deviation of 142 psi. Other tests indicate that the weakest bonds are obtained with such 24-hour storage. Storage for four hours and storage for three days have resulted in stronger bonds.

EXAMPLE 8

Forty-four bovine teeth were prepared as in Example 3, except that each was painted with a solution of 2½% phosphoric acid in water (not containing the aluminum oxalate) which was allowed to remain for sixty seconds and then washed away and dried. Next, a solution of 5% of an equilibrated mixture of sodium NTG-GMA and NTG-GMA in a mixture of 85% acetone and 15% water was applied and allowed to dry. Finally, a solution of 20% PMDM in a mixture of 85% acetone and 15% water was applied and allowed to dry. A cylinder of composite was bonded to each treated tooth surface and was stored in water at 37° C. Five samples were tested at four hours; five samples were tested at one day; five samples were tested at one week; five samples were tested at two weeks; and five samples were tested at thirty days. Results are shown below:

| Soak Time | 4 Hours | 1 Day | 1 Week | 2 Weeks | 30 Days |
|---|---|---|---|---|---|
| No. of Teeth | 14 | 5 | 15 | 5 | 5 |
| Average Bond Strength (psi) | 1139 | 1228 | 924 | 1094 | 1152 |
| Standard Deviation | 201 | 196 | 296 | 206 | 201 |

EXAMPLE 9

Twenty-eight bovine teeth were prepared as in Example 8, the only difference being that the initial mordant solution was 2½% phosphoric acid and ½% aluminum oxalate in water instead of the phosphoric acid alone. Samples were tested at four hours, one day and one week. Results are shown below:

| Soak Time | 4 Hours | 1 Day | 1 Week |
|---|---|---|---|
| No. of Teeth | 9 | 10 | 9 |
| Average Bond Strength (psi) | 1053 | 992 | 1088 |
| Standard Deviation | 180 | 152 | 244. |

EXAMPLE 10

Twenty bovine teeth were prepared as in Example 8 with the exception that the initial mordant solution was 2½% phosphoric acid, 1% nitric acid, and 0.5% aluminum oxalate in water. Samples were tested at one hour, one day, and one week. Results are shown below:

| Soak Time | 1 Hour | 1 Day | 1 Week |
|---|---|---|---|
| No. of Teeth | 10 | 5 | 5 |
| Average Bond Strength (psi) | 1424 | 1029 | 906 |
| Standard Deviation | 249 | 65 | 37. |

EXAMPLE 11

Ten bovine teeth were prepared as in Example 8 with the exception that the initial mordant solution was 5% phosphoric acid in water. Samples were tested at two hours and one day. Results are shown below:

| Soak Time | 2 Hours | 1 Day |
|---|---|---|
| No. of Teeth | 5 | 5 |
| Average Bond Strength (psi) | 1088 | 1128 |
| Standard Deviation | 328 | 94. |

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A method for preparing the surface of dentin, enamel, or other natural or industrial substrates containing or capable of binding metallic ions, for adhesion of composite materials or resins, which method comprises:
   (a) first contacting with the surface an aqueous solution comprising at least one strong acid or acidic salt,
   (b) then contacting with the surface a solution comprising a solvent and at least one compound selected from the group consisting of (1) N-phenylglycine in a mixture with the alkali metal salt of N-phenylglycine, (2) a mixture of the adduct of the alkali salts of N(p-tolyl)glycine and glycidyl methacrylate, with the adduct of N(p-tolyl)glycine and glycidyl methacrylate (3) the addition reaction product of the alkali metal salt of the addition reaction product of the alkali metal salt of N-phenylglycine and glycidyl methacrylate, and the addition reaction product of N-phenylglycine and glycidyl methacrylate, and (4) other amino acids each of which is combined in a mixture with an alkali metal salt thereof, wherein the alkali metal salt for each of said mixtures comprises between 40% and 60% of the total mixture, and
   (c) then contacting with the surface a solution comprising at least one monomer selected from the group consisting of (1) the addition reaction product of pyromellitic acid dianhydride and 2-hydroxyethyl methacrylate, (2) the addition reaction product of 3,3',4,4'-benzophenone tetracarboxylic dianhydride and 2-hydroxyethyl methacrylate, (3) 4-methacryloxyethyltrimelliticanhydride, and (4) other compounds containing at least one group or moiety capable of free radical polymerization and at least one aromatic ring or moiety containing electron-withdrawing substituents that do not interfere with free radical polymerization.

2. A method as in claim 1 wherein the strong acid is phosphoric acid and its concentration is from about 2 to 5%.

3. A method as in claim 1 wherein step (a) also includes an aqueous solution of at least one polyvalent cation, and an aqueous solution of at least one polyfunctional acid which can form relatively water-insoluble precipitates with calcium or polyvalent cations at pH values above that of the aqueous solution.

4. A method as in claim 3 wherein the polyvalent cation is selected from the group consisting of aluminum and ferric ions, used separately or together, and in concentration between about 0.00001% and saturation.

5. A method as in claim 4 wherein the strong acid is phosphoric acid.

6. A method as in claim 4 wherein the strong acid is a mixture of phosphoric and nitric acid.

7. A method as in claim 4 wherein the concentration of aluminum and ferric ions is between about 0.1% and about 5%.

8. A method as in claim 3 wherein the polyvalent cation and the polyfunctional acid consists of aluminum oxalate in a concentration better about one percent and 5 percent.

9. A method as in claim 3 wherein the polyfunctional acid is selected from the group consisting of oxalic, citric, pyruvic, tartaric, and other oligocarboxylic acids, used separately or in combinations, and in concentrations between about 0.00001% and saturation.

10. A method as in claim 9 wherein the concentration of polyfunctional acid is between about 1% and about 10%.

11. A method as in claim 3 wherein the strong acid is either phosphoric acid or a mixture of phosphoric acid and nitric acid and said polyvalent cation and the polyfunctional acid is aluminum oxalate.

12. A method as in claim 11 wherein the strong acid is either a water solution of phosphoric acid at about 2-5% or a mixture of phosphoric and nitric acid at about 2½% phosphoric acid and about 1% nitric acid, and said aluminum oxalate at about ½% in the water solution.

13. A method as claimed in claim 3 wherein at least one compound of (b) is selected from the group consisting of the mixture of sodium salts of N-phenylglycine, N(p-tolyl)glycine, N-phenylalanine, sarkosine, N-lauroylsarkosine, glycine, N,N-dimethylglycine, 3(N-phenyl) amino propionic acid, 3(N-p-tolyl) amino propionic acid, omega-amino fatty acids, N-substituted-omega-amino fatty acids, the addition reaction product of N-phenyl glycine and glycidyl reagents, the reaction product of N(substituted phenyl) glycine and glycidyl reagents, and other amino acids; and N-phenylglycine, N(P-toly)glycine, N(p-tolyl) glycine, N-phenylalanine, sarkosine, N-lauroylsarkosine, glycine, N,N-dimethylglycine, 3(N-phenyl)amino propionic acid, 3(N-p-tolyl)amino propionic acid, omega-amini fatty acids, N-substituted-omega-amino fatty acids, the addition reaction product of N-phenyl glycine and glycidyl reagents, the reaction product of N(substituted phenyl) glycine and glycidyl reagents, and other amino acids with the sodium salt in each of the said mixtures comprising between 40% and 60% of the total mixture; and wherein such compound or compounds, used separately or in combinations, are used in concentrations between about 0.1% and saturation.

14. A method as in claim 13 wherein the concentration in the solvent of the compound of (b) is between about 1% and about 10%.

15. A method as in claim 13 wherein the concentration of the compound of (b) is equal to or less than the normality of the strong acid of subpart (a)(1).

16. A method as in claim 3 wherein the compound of (b) is a mixture of the sodium salt of NPG (N-phenyl glycine), NPG-GMA (the addition reaction product of N-phenyl glycine and glycidyl methacrylate), or NTG-GMA (the adduct of N(p-tolyl)glycine and glycidyl methacrylate) with NPG, NPG-GMA, or NTG-GMA.

17. The method of claim 16 wherein the concentration of (b) is between 5% and 10%.

18. The method of claim 3 wherein the compound of (c) is PMDM (the addition reaction product of pyromellitic acid dianhydride and 2-hydroxyethyl methacrylate).

19. The method of claim 18 wherein the concentration of PMDM is between 5% and 20%.

20. A method as in claim 3 wherein the substrate surface is a dentin surface or an enamel surface.

21. A structure comprising a composite material or resin bonded to a dentin or enamel surface which has been prepared by the method of claim 3.

22. A method as in claim 1 wherein at least one compound of (b) is selected from the group consisting of the sodium salts of N-phenylglycine, N(p-tolyl) glycine, N-phenylalanine, sarkosine, N-lauroylsarkosine, glycine, N,N-dimethylglycine, 3(N-phenyl) amino propionic acid, (N-p-tolyl) amino propionic acid, omega-amino fatty acids, N-substituted-omega-amino fatty acids, the addition reaction product of N-phenyl glycine and glycidyl reagents, the reaction product of N(substituted phenyl) glycine and glycidyl reagents, and other amino acids; and wherein such compounds or compounds, used separately or in combinations, are used in concentrations between about 0.1% and saturation.

23. A method as in claim 22 wherein the concentration of the compound of (b) is between about 1% and about 10%.

24. A method as in claim 22 wherein the concentration of the compound of (b) is equal to or less than the normality of the strong acid of subpart (a)(1).

25. A method as in claim 1 wherein the compound of (b) is a mixture of the sodium salt of NPG, NPG-GMA, or NTG-GMA with the acid NPG (N-phenyl glycine), NPG-GMA (the addition reaction product of N-phenyl glycine and glycidyl methacrylate), or NTG-GMA (the adduct of N(p-tolyl)glycine and glycidyl methacrylate).

26. The method of claim 25 wherein the concentration of (b) is between 1% and 10%.

27. The method of claim 1 wherein the compound of (c) is PMDM (the addition reaction product of pyromellitic acid dianhydride and 2-hydroxyethyl methacrylate.

28. The method of claim 27 wherein the concentration of PMDM is between 5% and 20%.

29. A method as in claim 1 wherein the substrate surface is a dentin surface or an enamel surface.

30. A structure comprising a composite material or resin bonded to a dentin or enamel surface which has been prepared by the method of claim 1.

31. A method for preparing the surface of dentin, enamel, or other natural or industrial substrates containing or capable of binding metallic ions, for adhesion of composite materials or resins, which method comprises:
(a) first contacting with the surface an aqueous solution of (1) aluminum oxalate, and (2) phosphoric or nitric acid or a mixture of phosphoric and nitric acid,
(b) then contacting with the surface a solution comprising a solvent and at least one compound selected from the group consisting of (1) N-phenylglycine in a mixture with the alkali metal salt of N-phenylglycine, (2) a mixture of the adduct of the alkali salts N(p-tolyl)glycine and glycidyl methacrylate, with the mixture N(p-tolyl)glycine and glycidyl methacrylate (3) the addition reaction product of the alkali metal salt of N-phenylglycine and glycidyl methacrylate, (4) N-phenylglycine, N(p-tolyl) glycine, N-phenylalanine, sarkosine, N-lauroylsarkosine, glycine, N,N-dimethylglycine, 3(N-phenyl) amino propionic acid, 3(N-p-tolyl) amino propionic acid, omega-amino fatty acids, N-substituted-omega-amino fatty acids, the addition reaction product of N-phenyl glycine and glycidyl reagents, the reaction product of N(substituted phenyl) glycine and glycidyl reagents, and (5) other amino acids each of which is combined in a mixture with an alkali metal salt thereof, wherein the alkali metal salt for each of said mixtures comprises between 40% and 60% of the total mixture, and (c) then contacting the surface with a solution of PMDM (the addition reaction of pyromellitic acid dianhydride and 2-hydroxyethyl methacrylate).

32. The method of claim 31 wherein
the nitric acid concentration when used, is from about 1% to about 5%, the phosphoric acid and is from about 2% to 5%, and the aluminum oxalate concentration is from about ½% to about 10%,
the concentration of the compound of (b) is from about 1% to about 10%, and
the concentration of PMDM is for about 5% to about 20%.

33. The method of claim 32 wherein the acid-oxalate mixture is applied in water, while the compound of (b) and the PMDM are each applied in a mixture of 85% acetone and 15% water.

34. A structure comprising a composite material or resin bonded to the surface of a natural or industrial substrate which has been prepared by the method of claim 31.

35. An article of manufacture comprising in combination:
(a) a first container containing a composition comprising at least one strong acid,
(b) a second container containing one compound selected from the group consisting of (1) N-phenylglycine in a mixture with the alkali metal salt of N-phenylglycine, (2) a mixture of he adduct of the alkali salts N(p-tolyl)glycine and glycidyl methacrylate, with the mixture N(p-tolyl)glycine and glycidyl methacrylate (3) the addition reaction product of the alkali metal salt of N-phenylglycine and glycidyl methacrylate, (4) N-phenylglycine, N(p-tolyl) glycine, N-phenylalanine, sarkosine, N-lauroylsarkosine, glycine, N,N-dimethylglycine, 3(N-phenyl) amino propionic acid, 3(N-p-tolyl) amino propionic acid, omega-amino fatty acids, N-substituted-omega-amino fatty acids, the addition reaction product of N-phenyl glycine and glycidyl reagents, the reaction product of N(substituted phenyl) glycine and glycidyl reagents, and the other amino acids; and (5) other amino acids each of which is combined in a mixture with an alkali metal salt thereof, wherein the alkali metal salt for each of said mixtures comprises between 40% and 60% of the total mixture, and
(c) a third container containing a composition comprising at least one monomer selected from the group consisting of (1) the addition reaction product of pyromellitic acid dianhydride and 2-hydoxyethyl methacrylate, (2) the addition reaction product of 3,3',4,4'-benzophenoneytetracarboxylic dianhydride and 2-hydroxyethyl methacrylate, (3) 4-methacryloxyethyltrimellitic anhydride, and (4) other compounds containing at least one group or moiety capable of free radical polymerization and at least one aromatic ring or moiety containing electron-withdrawing substituents that do not interfere with free radical polymerization;
said containers being packaged together in said article of manufacture.

36. The article of claim 35 wherein said first container also contains a polyvalent ion and a polycarboxylic acid.

37. An article of manufacture as in claim 36 wherein the contents of the first, second, and third containers are in solutions.

38. An article of manufacture as in claim 35 wherein the contents of the first, second, and third containers are in solutions.

39. An article of manufacture comprising in combination:
(a) a first container containing phosphoric acid,
(b) a second container containing at least one compound selected from the group consisting of (1) N-phenylglycine in a mixture with the alkali metal salt of. N-phenylglycine, (2) a mixture of the adduct of the alkali salts N(p-tolyl)glycine and glycidyl methacrylate, with the mixture N(p-tolyl)glycine and glycidyl methacrylate (3) the addition reaction product of the alkali metal salt of N-phenylglycine and glycidyl methacrylate, (4) N-phenylglycine, N(p-tolyl) glycine, N-phenylalanine, sarkosine, N-lauroylsarkosine, glycine, N,N-dimethylglycine, 3(N-phenyl) amino propionic acid, 3(N-p-tolyl) amino propionic acid, omega-amino fatty acids, N-substituted-omega-amino fatty acids, the addition reaction product of N-phenyl glycine and glycidyl reagents, the reaction product of N(substituted phenyl) glycine and glycidyl reagents, and other amino acids; and (5) other amino acids each of which is combined in a mixture with an alkali metal salt thereof, wherein the alkali metal salt for each of said mixtures comprises between 40% and 60% of the total mixture, and
(c) a third container containing PMDM (the addition reaction product of pyromellitic acid dianhydride and 2-hydroxyethyl methacrylate),
said first and second and third containers being packaged together in said article of manufacture.

40. An article of manufacture as in claim 39 wherein the contents of the first, second and third containers are in solutions.

41. The article of claim 40 wherein solution (a) is phosphoric acid at 2-5% in water, solution (b) is at 5% to 10% in 85% acetone and 15% water, and solution (c) is at 5% to 20% in acetone.

42. An article of manufacture comprising in combination:
(a) a first container containing aluminum oxalate and either phosphoric acid or a mixture of phosphoric and nitric acids,
(b) a second container containing at least one compound selected from the group consisting of (1) N-phenylglycine in a mixture with the alkali metal salt of N-phenylglycine, (2) a mixture of the adduct of the salts of N(p-tolyl)glycine and glycidyl methacrylate, with the mixture N(p-tolyl)glycine and glycidyl methacrylate (3) the addition reaction product of the alkali metal salt of N-phenylglycine and glycidyl methacrylate, (4) N-phenylglycine, N(p-tolyl) glycine, N-phenylalanine, sarkosine, N-laurolysarkosine, glycine, N-N-dimethylglycine, 3(N-phenyl) amino propionic acid, 3(N-p-tolyl) amino propionic acid, omega-amino fatty acids, N-substituted-omega-amino fatty acids, the addition reaction product of N-phenyl glycine and glycidyl reagents, the reaction product of N(substituted phenyl) glycine and glycidyl reagents, and other amino acids; and (5) other amino acids each of which is combined in a mixture with an alkali metal salt thereof, wherein the alkali metal salt for each of said mixtures comprises between 40% and 60% of the total mixture, and (c) a third container containing PMDM (the addition reaction product of pyromellitic acid anhydride and 2-hydroxyethyl methacrylate), said first and second and third containers being packaged together in said article of manufacture.

43. An article of manufacture as in claim 42 wherein the contents of the first, second and third containers are in solutions.

44. The article of claim 43 wherein solution (a) is phosphoric acid at 2–5% in water, solution (b) is at 5% to 10% in 85% acetone and 15% water, and solution (c) is at 5% to 20% in acetone.

* * * * *

UNITED STATES PATENT AND TRADEMARK OFFICE
CERTIFICATE OF CORRECTION

PATENT NO. : 4,964,911

DATED : October 23, 1990

INVENTOR(S) : Ibsen, Robert L. et al

It is certified that error appears in the above-identified patent and that said Letters Patent is hereby corrected as shown below:

On the title page in the Related U.S. Application Data, [63]
"Ser. No. 107102," should read --Ser. No. 107,012--.

Column 4, line 56, delete "aqueous".
Column 6, line 51, "A solution" should read --A 10% solution--.
Column 11, line 10, "better" should read --between--.
Column 11, line 45, "omega-amini" should read --omega-amino--.
Column 12, line 17, "(N-p-tolyl)" should read --3(N-p-tolyl)--.
Column 13, line 15, "reaction of" should read --reaction product of--.
Column 13, line 65, "benzophenoneytetracarboxylic" should read
--benzophenoetetracarboxylic--.
Column 14, line 62, "of the salts of" should read --of the alkali salts of--.
Column 14, line 68, "N-laurolysarkosine" should read --lauroylsarkosine--.

Signed and Sealed this

Second Day of June, 1992

Attest:

DOUGLAS B. COMER

Attesting Officer

Acting Commissioner of Patents and Trademarks